(12) United States Patent
Hanes, II

(10) Patent No.: US 10,603,074 B2
(45) Date of Patent: Mar. 31, 2020

(54) DISSECTION AND RETRACTION DEVICE FOR VAGINAL SACRAL COLPOPEXY

(71) Applicant: Boston Scientific Scimed, Inc., Maple Grove, MN (US)

(72) Inventor: Charles R. Hanes, II, Mobile, AL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1029 days.

(21) Appl. No.: 14/640,887

(22) Filed: Mar. 6, 2015

(65) Prior Publication Data

US 2015/0173796 A1    Jun. 25, 2015

Related U.S. Application Data

(63) Continuation of application No. 12/760,055, filed on Apr. 14, 2010, now Pat. No. 8,998,803.

(60) Provisional application No. 61/214,960, filed on Apr. 30, 2009.

(51) Int. Cl.
*A61B 17/42* (2006.01)
*A61B 17/02* (2006.01)
(Continued)

(52) U.S. Cl.
CPC .......... *A61B 17/42* (2013.01); *A61B 17/0218* (2013.01); *A61B 17/0206* (2013.01); *A61B 17/3462* (2013.01); *A61F 2/0045* (2013.01)

(58) Field of Classification Search
CPC ...... A61F 2/0031; A61F 2/0036; A61F 2/004; A61F 2/0045; A61F 2/0063; A61F 2002/0072; A61B 2017/0218
See application file for complete search history.

(56) References Cited

U.S. PATENT DOCUMENTS 1,222,478 A    4/1917   Sheaff
5,209,754 A    5/1993   Ahluwalia
(Continued)

FOREIGN PATENT DOCUMENTS

DE    4115548 A1   11/1991
EP    2424452 A1   3/2012
(Continued)

OTHER PUBLICATIONS

Wheeless, Jr. et al. "Sacrospinous Ligament Suspension of the Vagina" Atlas of Pelvic Surgery. Aug. 3, 2008. http://www.atlasofpelvicsurgery.com/2VaginalandUrethra/3SacrospinousLigamentSuspensionoftheVagina/chap2sec3.html.*
(Continued)

*Primary Examiner* — Carrie R Dorna
(74) *Attorney, Agent, or Firm* — Brake Hughes Bellermann LLP

(57) ABSTRACT

In one embodiment the apparatus includes a first retractor, a second retractor, and a shaft. The shaft defines a central channel extending from a first end portion of the shaft to a second end portion of the shaft. The first retractor and the second retractor are configured to collectively form a lumen. The shaft is configured to be disposed within the lumen. In one embodiment method of disposing a graft within a body of a patient, includes making an incision in the body of the patient, inserting a medical device into the body of the patient through the incision, removing the shaft of the medical device from the body of the patient, and moving the first refractor within the body of the patient away from the second retractor.

15 Claims, 2 Drawing Sheets

(51) Int. Cl.
*A61F 2/00* (2006.01)
*A61B 17/34* (2006.01)

(56) References Cited

U.S. PATENT DOCUMENTS

| | | | |
|---|---|---|---|
| 5,304,187 | A | 4/1994 | Green et al. |
| 5,354,292 | A | 10/1994 | Braeuer et al. |
| 5,843,108 | A | 12/1998 | Samuels |
| 5,976,146 | A * | 11/1999 | Ogawa ............ A61B 17/00234 604/174 |
| 6,126,594 | A | 10/2000 | Bayer |
| 6,235,037 | B1 | 5/2001 | East et al. |
| 6,245,082 | B1 * | 6/2001 | Gellman .......... A61B 17/00234 600/29 |
| 6,315,713 | B1 | 11/2001 | Takada |
| 6,319,272 | B1 | 11/2001 | Brenneman et al. |
| 6,364,832 | B1 | 4/2002 | Propp |
| 6,423,075 | B1 | 7/2002 | Singh et al. |
| 6,572,631 | B1 | 6/2003 | McCartney |
| 6,592,515 | B2 | 7/2003 | Thierfelder et al. |
| 6,712,795 | B1 | 3/2004 | Cohen |
| 6,755,781 | B2 | 6/2004 | Gellman |
| 6,884,212 | B2 | 4/2005 | Thierfelder et al. |
| 6,936,052 | B2 | 8/2005 | Gellman et al. |
| 6,953,428 | B2 | 10/2005 | Gellman et al. |
| 6,991,597 | B2 | 1/2006 | Gellman et al. |
| 7,025,063 | B2 | 4/2006 | Snitkin et al. |
| 7,025,772 | B2 | 4/2006 | Gellman et al. |
| 7,070,558 | B2 | 7/2006 | Gellman et al. |
| 7,235,043 | B2 | 6/2007 | Gellman et al. |
| 7,867,222 | B1 | 1/2011 | Tilton, Jr. et al. |
| 7,874,982 | B2 | 1/2011 | Selover et al. |
| 8,454,644 | B2 | 6/2013 | McDonnell |
| 8,734,319 | B2 | 5/2014 | Hanes, II |
| 2002/0028980 | A1 | 3/2002 | Thierfelder et al. |
| 2002/0107525 | A1 * | 8/2002 | Harari ................ A61B 17/0401 606/104 |
| 2002/0123668 | A1 | 9/2002 | Ritland |
| 2003/0236447 | A1 | 12/2003 | Ritland |
| 2004/0093001 | A1 | 5/2004 | Hamada |
| 2004/0230092 | A1 | 11/2004 | Thierfelder et al. |
| 2005/0038462 | A1 | 2/2005 | Lubock et al. |
| 2005/0065395 | A1 | 3/2005 | Mellier |
| 2005/0107805 | A1 | 5/2005 | Bouffier et al. |
| 2005/0216013 | A1 | 9/2005 | Dallara |
| 2006/0173483 | A1 | 8/2006 | Kieturakis et al. |
| 2006/0212046 | A1 | 9/2006 | Pearce |
| 2006/0229656 | A1 * | 10/2006 | McDonnell ............ A61M 29/00 606/191 |
| 2006/0260618 | A1 | 11/2006 | Hodroff |
| 2007/0219416 | A1 | 9/2007 | Perez-Cruet |
| 2008/0132754 | A1 * | 6/2008 | Thierfelder ...... A61B 17/00234 600/37 |
| 2008/0207988 | A1 | 8/2008 | Hanes |
| 2008/0275306 | A1 | 11/2008 | Rebuffat |
| 2009/0005646 | A1 | 1/2009 | Nowitzke et al. |
| 2009/0099422 | A1 | 4/2009 | George |
| 2010/0280627 | A1 | 11/2010 | Hanes |
| 2011/0208226 | A1 | 8/2011 | Fatone |

FOREIGN PATENT DOCUMENTS

| | | |
|---|---|---|
| WO | 1996/027332 A1 | 9/1996 |
| WO | 2002/019946 A2 | 3/2002 |
| WO | 2002/098301 A1 | 12/2002 |
| WO | 2005/110273 A1 | 11/2005 |
| WO | 2010/126718 A1 | 11/2010 |

OTHER PUBLICATIONS

International Search Report and Written Opinion received for Application Serial No. PCT/US2010/031271, dated Jul. 2, 2010, 16 pages.

Non-Final Office Action for U.S. Appl. No. 12/039,488, dated Nov. 9, 2011, 15 pages.

Non-Final Office Action for U.S. Appl. No. 12/039,488, filed Feb. 8, 2012, 10 pages.

Non-Final Office Action for U.S. Appl. No. 12/039,488, dated Jul. 8, 2013, 19 pages.

Office Action for Canadian Patent Application No. 2,679,392, dated May 27, 2014, 2 pages.

Notice of Allowance for U.S. Appl. No. 12/039,488, dated Jan. 15, 2014, 9 pages.

Final Office Action for U.S. Appl. No. 12/039,488, dated Apr. 6, 2012, 19 pages.

Response to Final Office Action for U.S. Appl. No. 12/039,488, filed Jun. 5, 2012, 11 pages.

First Examiners Report for Australian Patent Application No. 2008221334, dated Jul. 19, 2012, 3 pages.

Vander Weiden, R. M. F., et al., "A New Device for Bone Anchor Fixation in Laparoscopic Sacrocolpopexy: The 15 Franciscan Laparoscopic Bone Anchor Inserter", Surgical Endoscopy and Other Interventional Techniques, vol. 19, No. 4, Apr. 2005, pp. 594-597.

Visco, et al., "Vaginal Mesh Erosion After Abdominal Sacral Colpopexy", American Journal of Obstetric Gynecology, vol. 184, Feb. 2001, pp. 297-302.

medcompare.com, "Prolene and polyester mesh", available on line at< http://www.medcompare.com/details/358621/prolene-polypropylene> retrieved on Jun. 25, 2008, 4 pages.

Nygaard, et al., "Abdominal Sacrocolpopexy: A Comprehensive Review", Obstetrics & Gynecology, vol. 104, No. 4, Oct. 2004, pp. 805-823.

ProTrak 5 mm (Single Use Instrument), Description of product: ProTrak 5 mm (Single Use Instrument), Autosuture-Advancing Possibilities in Surgery, http:www.autosuture.com (Jun. 25, 2008).

Ross, Jim W., "Techniques of Laparoscopic Repair of Total Vault Eversion After Hysterectomy", Journal of the American Association of Gynecological Laparoscopy, vol. 4, No. 2, Feb. 1997, pp. 173-183.

Sze, et al.,"Transvaginal Repair of Vault Prolapse: A Review", Obstetrics & Gynecology, vol. 89, No. 3, Mar. 1997, pp. 466-475.

Barber, et al., "Bilateral Uterosacral Ligament Vaginal Vault Suspension With Site-Specific Endopelvic Fascia Defect Repair for Treatment of Pelvic Organ Prolapse", American Journal of Obstetric Gynecology, vol. 183, No. 6,Dec. 2000, pp. 1402-1411.

Benson, et al., "Vaginal Versus Abdominal Reconstructive Surgery for the Treatment of Pelvic Support Defects: A Prospective Randomized Study with Long-Term Outcome Evaluation", American Journal of Obstetric Gynecology, vol. 175, Dec. 1996, pp. 1418-1422.

Cundiff, et al., "Abdominal Sacral Colpoperineopexy: A New Approach for Correction of Posterior Compartment Defects and Perineal Descent Associated with Vaginal Vault Prolapse", American Journal of Obstetric Gynecology, vol. 177, No. 6, Dec. 1997, pp. 1345-1355.

Ellioti, et al., "Long-Term Results of Robotic Assisted Laparoscopic Sacrocolpopexy for the Treatment of High Grade Vaginal Vault Prolapse", Journal of Urology, vol. 176, No. 2, Aug. 2006, pp. 655-659.

"Definition of the Term Cannulate", retrieved <www.thefreedictionary.com/Cannulate>, retrieved on Apr. 1, 2014, 2 pages.

"Definition of the Term unitary", retrieved <www.thefreedictionary.com/unitary>,retrieved on Apr. 2, 2014, 2 pages.

Silva, et al., "Uterosacral Ligament Vault Suspension: Five-Year Outcomes", Obstetrics & Gynecology, vol. 108, No. 2, Aug. 2006, pp. 255-263.

Su, et al., "Abdominovaginal Sacral Colpoperineopexy: A Quality of Life Assessment", Journal of Pelvic Medicine & Surgery, vol. 13, No. 4, Jul./Aug. 2007, pp. 181-190.

Shull, et al., "A Transvaginal Approach to Repair of Apical and Other Associated Sites of Pelvic Organ Prolapse with Uterosacral Ligaments", American Journal of Obstetric Gynecology, vol. 183, No. 6, Dec. 2000, pp. 1365-1374.

Flynn, et al., "Abdominal Surgery for Pelvic Organ Prolapse", Journal of Pelvic Medicine & Surgery, vol. 13, No. 4, Jul./Aug. 2007, pp. 157-170.

(56) References Cited

OTHER PUBLICATIONS

Hall, et al., "Laparoscopic Sacrocolpopexy: Lessons Learned", Journal of Pelvic Medicine and Surgery, vol. 13, No. 4, Jul./Aug. 2007, pp. 197-201.

Karram, et al., "High Uterosacral Vaginal Vault Suspension with Fascial Reconstruction for Vaginal Repair of Enterocele and Vaginal Vault Prolapse", American Journal of Obstetric Gynecology, vol. 185, No. 6, Dec. 2001 , pp. 1339-1343.

Maher, et al., "Abdominal Sacral Colpopexy or Vaginal Sacrospinous Colpopexy for Vaginal Vault Prolapse: A Prospective Randomized Study", American Journal of Obstetric Gynecology, vol. 190, No. 1, Jan. 2004, pp. 20-26.

Morley, et al., "Sacrospinous Ligament Fixation for Eversion of the Vagina", American Journal of Obstetric Gynecology, vol. 158, No. 5, Apr. 1988, pp. 872-881.

Nezhat, et al., "Robotic-Assisted Laparoscopy in Gynecological Surgery", Scientific Paper, Journal of the Society of Laparoendoscopic Surgeons, vol. 10, No. 3, 2006, pp. 317-320.

International Preliminary Report on Patentability for PCT Patent Application No. PCT/US2010/031271, dated Nov. 10, 2011, 8 pages.

Office Action Response for Canadian Patent Application No. 2,679,392, filed on Nov. 26, 2014, 14 pages.

Communication pursuant to Rules 161(1) and 162 EPC for EP Patent Application No. 10718761.9, dated Dec. 9, 2011, 2 pages.

Examination Notification Art. 94(3) for EP Patent Application 10718761.9, dated Oct. 19, 2012, 4 pages.

Examination Notification Art. 94(3) Response for EP Patent Application 10718761.9, filed on Dec. 18, 2012, 6 pages.

Restriction Requirement for U.S. Appl. No. 12/039,488, dated Sep. 14, 2011, 7 pages.

Notice of Allowance for Canadian Patent No. 2,679,392, dated Jan. 22, 2015, 1 page.

Response to Non-Final Office Action for U.S. Appl. No. 12/039,488, filed Oct. 8, 2013, 8 pages.

Non-Final Office Action received for U.S. Appl. No. 12/039,488, dated Jul. 8, 2013, 19 pages.

\* cited by examiner

DISSECTION AND RETRACTION DEVICE FOR VAGINAL SACRAL COLPOPEXY

CROSS REFERENCE TO RELATED APPLICATIONS

This application is a Continuation of, and claims priority to, U.S. patent application Ser. No. 12/760,055, filed on Apr. 14, 2010, entitled "DISSECTION AND RETRACTION DEVICE FOR VAGINAL SACRAL COLPOPEXY", which, in turn, claims priority to U.S. Patent Application No. 61/214,960, filed on Apr. 30, 2009, entitled "DISSECTION AND RETRACTION DEVICE FOR VAGINAL SACRAL COLPOPEXY", the disclosures of which are incorporated by reference herein in their entirety.

BACKGROUND

This invention enables a sacral colpopexy operation to be performed by means of vaginal surgery. Traditionally, this operation has been performed through an abdominal incision.

The abdominal sacral colpopexy (ASC) is widely recognized as the "gold standard" of all operations for the correction of vaginal vault prolapse. However, there are a large number of surgeons that advocate vaginal surgery using surgical procedures and devices that suspend the vagina to the uterosacral or sacrospinous ligaments. They point to studies showing that vaginal surgery~in general, is easier for the patient to recover from and often has lower operative morbidity than the abdominal operations.

Clinical studies comparing ASC with the vaginal procedures have indicated greater success with the ASC and a lower failure rate, but the ASC does carry a higher complication rate.

If the sacral colpopexy operation can be performed using a vaginal technique that does not deviate from the optimal abdominal technique, then the advantages of being able to offer the gold standard operation will be enhanced by avoiding those aspects of abdominal surgery that are unattractive both to surgeons and patients. In addition, if this can be done in a fashion that is technically safe and easy, it is anticipated that many surgeons would incorporate this into their standard practice.

One of the technical challenges of the sacral colpopexy is to avoid the middle sacral vessels when fixing the graft to the presacral fascia. This instrument enables visualization of these vessels thereby providing the ability to fix the graft at a safe distance from the vessels.

This instrument is a modification of the instrument previously filed (U.S. patent application Ser. No. 12/039,488). This modification results in the sleeve used to house the dissecting instrument being in two pieces rather than one. These two pieces, when approximated, from the channel through which the dissecting instrument slides. When the dissecting instrument is removed, the two pieces are then used as retractors enabling direct visualization of the operative field. The distal ends of these retractors would be in close proximity to the sacrum and would expose the presacral fascial sheath so that the graft material could then be fixed to this fascial sheath under direct visualization. The use of these retractors takes the place of the operating instrument described in U.S. patent application Ser. No. 12/039,488.

SUMMARY

The invention enables the operating surgeon to create a tunnel from the vaginal apex to the sacrum while remaining in the retroperitoneal space and to identify the middle sacral vessels before fixation of the graft material to the sacrum or presacral fascia. The graft may then be safely fixed using sutures, helical tacks or bone anchors.

This provides the patient with certain distinct advantages. She is able to have the "gold standard" operation using a vaginal technique that does not deviate from the accepted, optimal abdominal technique in any way other than the approach to the operative site. She, therefore, may benefit from the advantages of vaginal surgery as compared with abdominal surgery, quicker recovery and less surgical morbidity.

This invention also provides the surgeon with distinct advantages. He/she is able to offer the patient a surgical repair that is the "gold standard" and can be done quicker than the ASC.

Another advantage is that with this vaginal approach, the posterior compartment can be repaired through the same incision. By contrast, in the ASC procedure, if a posterior compartment defect exists, the surgeon would normally have to make a separate vaginal incision after completing the ASC to perform the repair.

DETAILED DESCRIPTION

Figure 1:
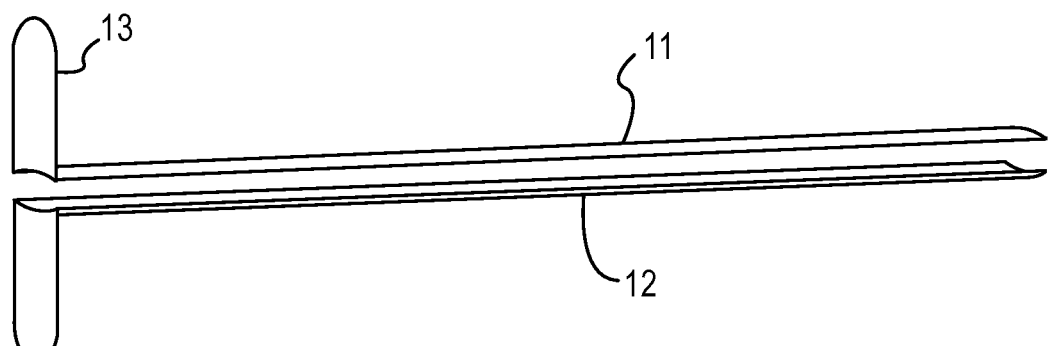
FIG. 1 is a perspective view from the user's right side of the retraction device.
Figure 2:
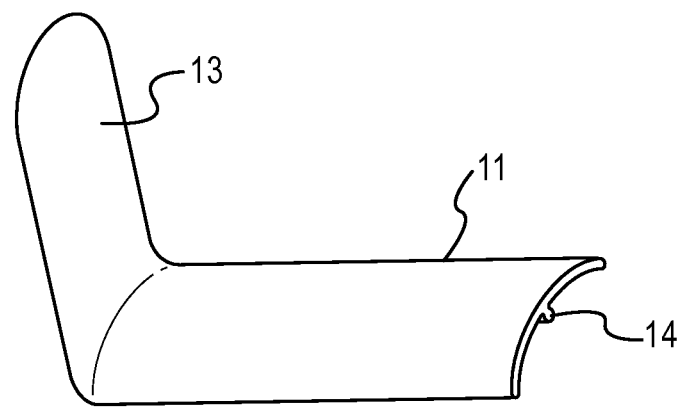
FIG. 2 is another view of one blade of the retraction device.

FIGS. 1 and 2 are perspective views from the user's right side of the retraction devices. The anterior blade 11 and the posterior blade 12 have handles 13. There may be a ridge 14 running down the midline of the inner surface of the blades. In one embodiment, the blades are long enough to reach from the vaginal opening to the sacral promontory.

Figure 3:
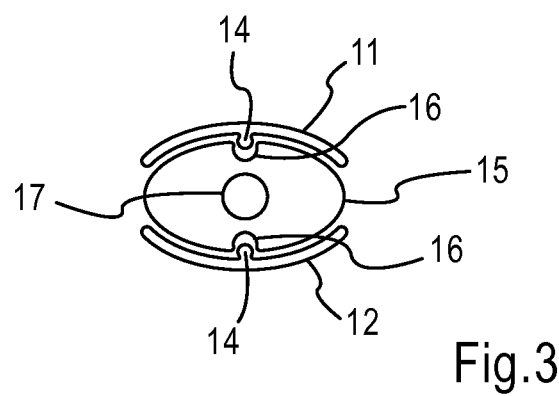
FIG. 3 is a perspective cross-sectional of the dissecting instrument and the retraction blades.

FIG. 3 shows the blades 11, 12 and the dissecting device 15. Note that the curvature of the blades is identical with the curvature on the anterior and posterior surfaces of the dissecting instrument. The blades may have a ridge on their inner surface 14 which slide into a corresponding groove 16 on the anterior and posterior surfaces of the dissecting instrument 15. This ridge and groove system enables the blades and the dissecting device to be inserted as one piece without separation. The central channel 17 in the dissection device allows for the insertion of a separate suction/irrigation instrument that is utilized for the creation of the tunnel in the soft tissue by hydrodissection as would be the case if a space were being created between the apex of the vagina and the sacrum.

Figure 4:
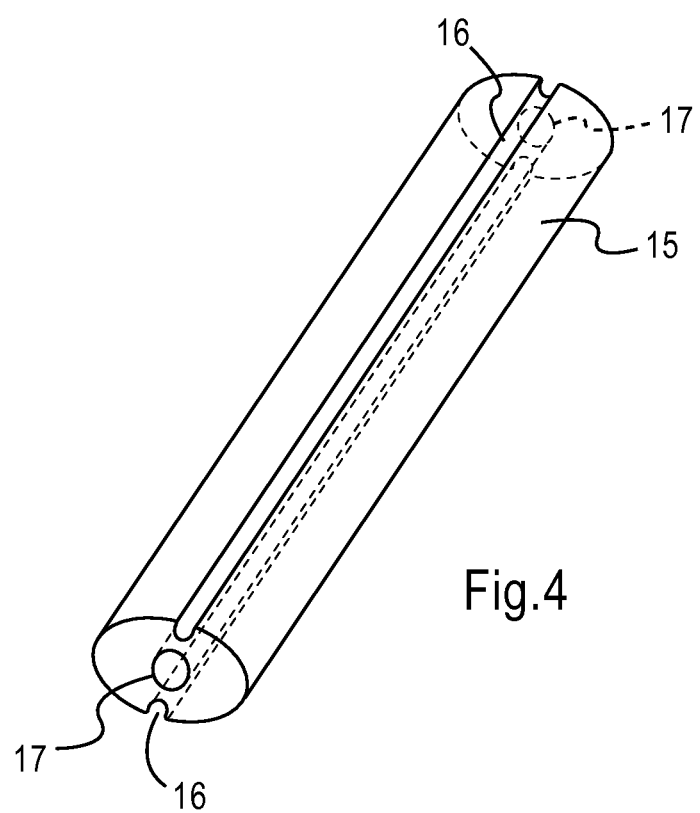
FIG. 4 is a perspective view from the user's right side of the dissection instrument.

FIG. 4 is a perspective views from the user's right side of the dissecting instrument 15. This instrument may be elliptical, circular or any combination of these shapes. Grooves 16 are seen on the anterior and the posterior surfaces. The central channel 17 traverses the full length of the instrument.

REFERENCE NUMERALS

11—Anterior blade
12—Posterior blade
13—Handle

14—Ridge on inner surface of blade
15—Dissecting instrument
16—Groove on dissecting instrument
17—Central channel of dissecting instrument Operation Prior to using the instrument, an incision will have been made in the vagina. The length of this incision is sufficient to accommodate the cross-sectional area of the instrument. Usually, this incision would be in the posterior vaginal wall although the anterior wall could also be used. The perirectal space between the rectum and vagina is developed usually with the aid of hydrodissection. This space is created up to the level of the vaginal apex and out laterally to the right pelvic sidewall.

The retractor blades 11, 12 are articulated to the dissecting instrument 15 by sliding the ridges 14 of the blades into the grooves 16 of the dissecting instrument. The end of the instrument is then inserted into the incision. Using hydrodissection through the central channel 17 of the dissecting instrument, a space is created between the vaginal apex and the sacrum. The instrument is advanced progressively to the sacrum as this space is created.

When the sacral promontory is reached, the dissecting instrument 15 is withdrawn by sliding it back out of the vagina leaving the retractor blades 11, 12 in place. The operating surgeon may then grasp the handles 13 of the blades and retract the blades in opposite directions from one another thereby exposing a larger area in front of the sacrum. With adequate direct lighting between the blades, this presacral space can be visualized. The tissue overlying the presacral fascia can be dissected off of the surface of the fascia using routine surgical techniques. The middle sacral vessels are identified so that a piece of graft material can be safely attached to the presacral fascia without causing significant bleeding.

When this fixation has been accomplished to the satisfaction of the operating Surgeon~the retractor blades 11, 12 are withdrawn. Upon complete removal of the Instrument~the graft remains in the operative field. One end is fixed to the sacrum while the other extends out of the vaginal incision. The remaining part of the sacral colpopexy procedure is completed by trimming the length of the graft and fixing it to the outer surfaces of the vagina using standard techniques.

Another incision may be made in the anterior vagina and a space created between the bladder and vagina as far as the vaginal apex. The two incisions may be joined around the apex. A piece of graft material may then be attached to the previously positioned piece and then attached to the outer surface of the anterior vagina, again using standard suture techniques.

Other Variations

The groove and ridge system that enables the retractor blades to be attached to the dissecting instrument is only one way to accomplish this articulation of the blades to the instrument. Any number of other modes of attachment could be used with the objective being to be able to insert the combination of the dissecting instrument and retractor blades as one piece. Disarticulation and withdrawal of the dissecting instrument from the blades then enables visualization of the presacral space and completion of the procedure.

Although, the operation described here is a sacral colpopexy, this instrument can also be used for a rectopexy in female patients as well as any other procedure requiring tunneling through soft tissue and direct visualization of the operative site.

What is claimed is:

1. A method of disposing a graft within a body of a patient, comprising:
    making an incision in the body of the patient;
    inserting a medical device into the body of the patient through the incision, the medical device including a first retractor having a curved surface, a second retractor having a curved surface, and a dissecting device disposed between the first retractor and the second retractor, the curved surfaces of the first retractor and the second retractor being complimentary to a surface of the dissecting device, the first retractor includes a ridge on the curved surface of the first retractor, the second retractor includes a ridge on the curved surface of the second retractor, the dissecting device includes a first groove on the surface of the dissecting device so as to receive the ridge of the first retractor and a second groove on the surface of the dissecting device so as to receive the ridge of the second retractor;
    removing the dissecting device of the medical device from the body of the patient; and
    moving the first retractor within the body of the patient away from the second retractor.

2. The method of claim 1, further comprising:
    positioning the medical device within the body of the patient to a location proximate an attachment location.

3. The method of claim 1, further comprising:
    identifying blood vessels proximate an attachment location after the moving.

4. The method of claim 1, wherein the making an incision in the body of the patient includes making a vaginal incision.

5. The method of claim 1, wherein the making an incision in the body of the patient includes making a posterior incision.

6. The method of claim 1, further comprising:
    positioning the medical device within the body of the patient to a location proximate a fixation site; and
    coupling a graft to the fixation site.

7. The method of claim 1, further comprising:
    positioning the medical device within the body of the patient to a location proximate a sacrum of the patient.

8. The method of claim 1, further comprising:
    positioning the medical device within the body of the patient to a location proximate a sacrum of the patient; and
    coupling a graft to the sacrum of the patient.

9. The method of claim 1, further comprising:
    positioning the medical device within the body of the patient to a location proximate a sacrum of the patient;
    coupling a first portion of a graft to the sacrum of the patient; and
    coupling a second portion of the graft to an outer surface of a vagina of the patient.

10. The method of claim 1, wherein the making an incision in the body of the patient includes making a posterior vaginal incision, the method further comprising:
    positioning the medical device within the body of the patient to a location proximate a sacrum of the patient;
    coupling a first portion of a first graft to the sacrum of the patient;
    coupling a second portion of the first graft to an outer surface of a vagina of the patient;
    making an anterior vaginal incision;

coupling a first portion of a second graft to the first graft; and coupling a second portion of the second graft to an outer surface of an anterior portion of the vagina of the patient.

11. The method of claim 1, wherein the dissecting device includes a lumen extending from a first end portion of the dissecting device to a second end portion of the dissecting device.

12. The method of claim 1, wherein removing the dissecting device includes sliding the dissecting device out from the body of the patient.

13. The method of claim 1, further comprising a handle member at a proximal end of each of the first retractor and the second retractor, the handle member extending transversely to at least one of the first retractor or the second retractor.

14. The method of claim 1, further comprising sliding the ridge of the first retractor into the first groove of the dissecting device.

15. The method of claim 1, further comprising sliding the ridge of the second retractor into the second groove of the dissecting device.

* * * * *